United States Patent [19]

Merkel et al.

[11] 4,193,195

[45] Mar. 18, 1980

[54] ORTHODONTIC APPLIANCE

[75] Inventors: Daniel A. Merkel; John E. Viglietti; William P. Gagin, all of Sheboygan, Wis.

[73] Assignee: American Orthodontics Corporation, Sheboygan, Wis.

[21] Appl. No.: 926,287

[22] Filed: Jul. 20, 1978

[51] Int. Cl.² .............................................. A61C 7/00
[52] U.S. Cl. ..................................................... 433/13
[58] Field of Search ......................................... 32/14 A

[56] References Cited

U.S. PATENT DOCUMENTS

| 3,028,671 | 4/1962 | Berger | 32/14 A |
| 3,256,602 | 6/1966 | Broussard et al. | 32/14 A |
| 3,793,730 | 2/1974 | Begg | 32/14 A |

Primary Examiner—Robert Peshock
Attorney, Agent, or Firm—Lloyd L. Zickert

[57] ABSTRACT

An orthodontic appliance to be used in a straight-wire technique setup as an auxiliary for applying closing forces between spaced teeth, wherein the appliance is mounted on a bracket attached to a band or pad. The appliance includes a base attachable to the bracket and an arm extending from the base and terminating in a hook for the attachment thereto of a force transmission member, such as an elastic. The appliance is attached to the bracket so that it is removable from the bracket after the use of the appliance has been completed and while the bracket remains mounted on a tooth.

9 Claims, 12 Drawing Figures

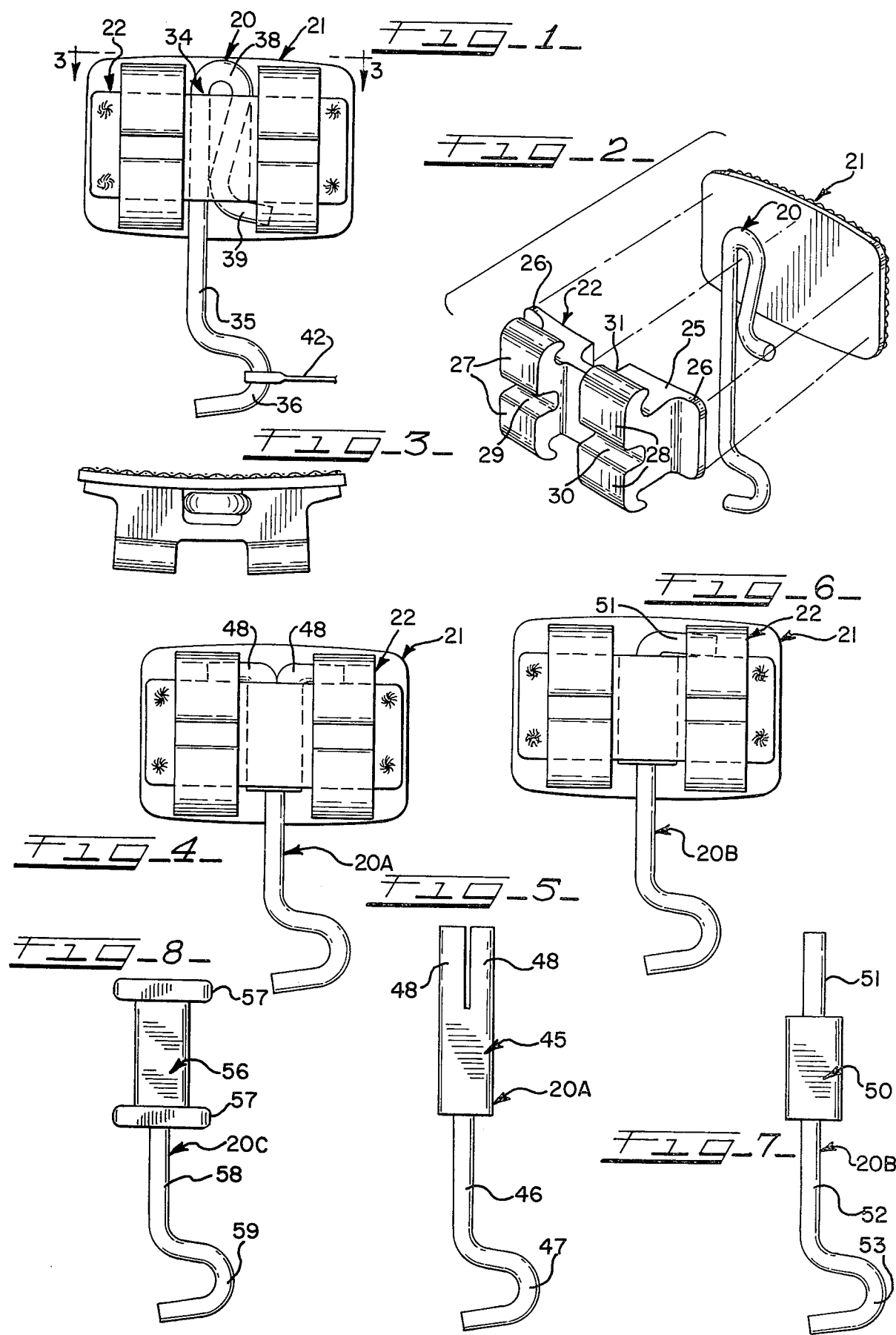

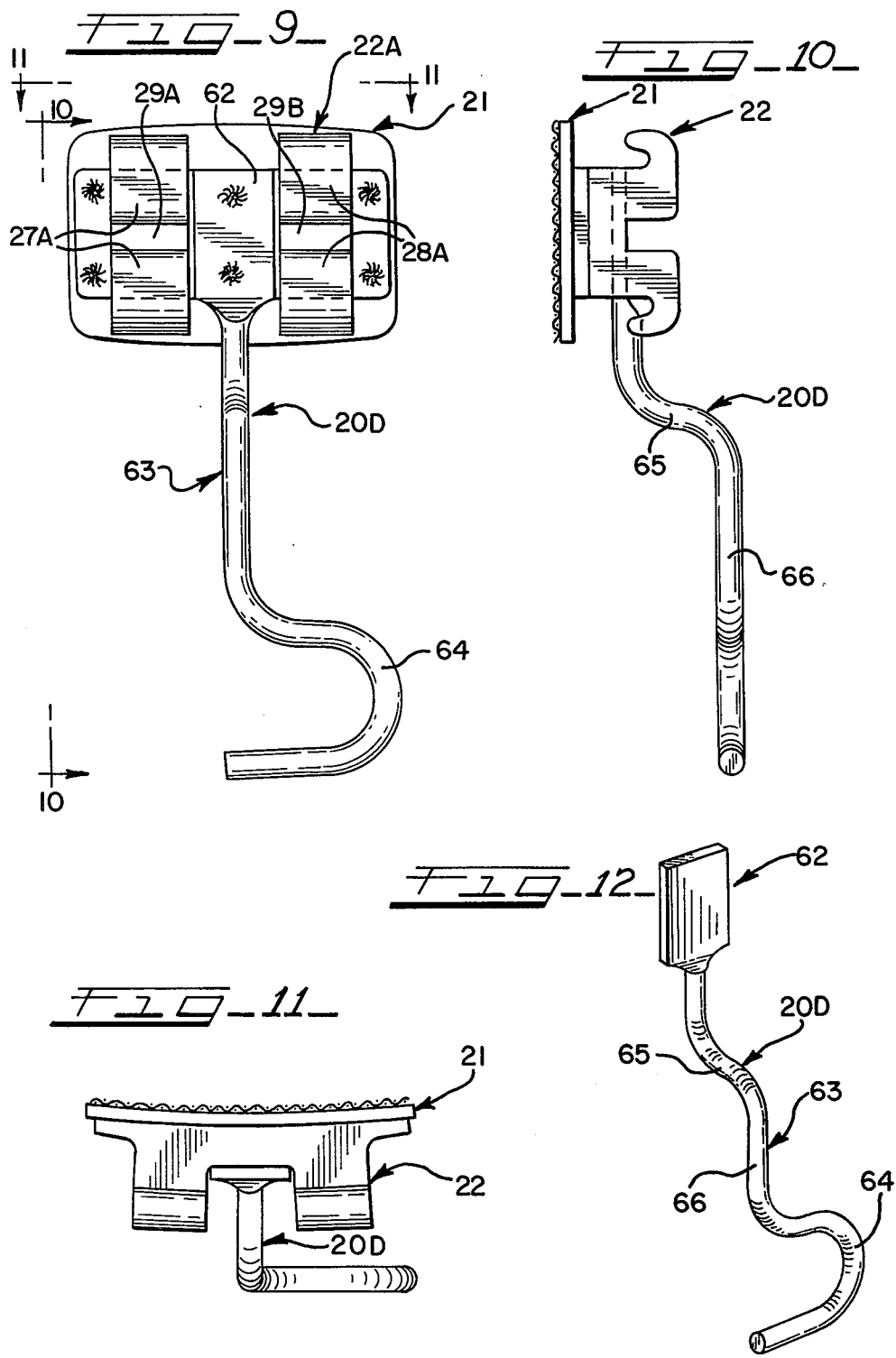

ORTHODONTIC APPLIANCE

This invention relates in general to an orthodontic appliance to be mounted on a bracket but being removable therefrom and to provide an arm extending from the bracket to have the force applied to the arm for movement of the tooth on which the bracket is mounted.

The appliance of the present invention concerns the situation in the treatment of a patient with the straight-wire technique of closing spaces and particularly spaces left by extraction sites. Heretofore, such closing of spaces has been accomplished in this technique by use of the integral building of an arm into brackets. The arm extends gingivally from the bracket and is provided with a hook onto which an elastic member for applying a force can be attached. Thereafter, following the closing of the spaces when it is desired to apply other forces to the tooth having the bracket with the arm thereon and the arm is no longer needed for treatment, it is necessary to remove the bracket with the arm and replace it with another bracket not having an arm for effecting further treatment. Valuable time on the part of the orthodontist is required for changing brackets.

The present invention relates to an appliance that can be selectively used on all conventional edgewise brackets when needed for applying a closing force to a tooth through an arm extending from the bracket. Orthodontists having the usual supply of brackets can add the appliance of the invention to the brackets with the usual equipment of their office. More particularly, the appliance of the present invention includes an arm having a base mountable on a bracket and an arm extending from the base with a hook at the free end receiving an elastic force transmission member. Further, the base of the appliance is mountable on the bracket so that once the bracket is mounted on a tooth, it can be removed from the bracket between stages of treatment without removal of the bracket from the tooth. Thereafter, the bracket can be used in the manner desired by the orthodontist for effecting further treatment of the teeth. The appliance of the present invention may take any of several forms, but it is important to remember that the appliance, after being attached to a bracket, can be removed during treatment without removal of the bracket from the tooth or destroyng the integrity of the bracket.

It is therefore an object of the present invention to provide a new and improved orthodontic appliance for use with brackets to apply closing forces between teeth, wherein the appliance may be selectively mounted on any bracket, and thereafter during treatment removed from the bracket without removing the bracket from the tooth.

A further object of the present invention is to provide an orthodontic appliance in the form of an arm that extends along the occlusogingival axis of a bracket mounted on a tooth, and wherein the arm may be mounted on a standard bracket prior to mounting the bracket onto the tooth and thereafter removed from the bracket without removing the bracket from the tooth.

Other objects, features and advantages of the invention will be apparent from the following detailed disclosure, taken in conjunction with the accompanying sheets of drawings, wherein like reference numerals refer to like parts, in which:

FIG. 1 is a front elevational view of a bracket and pad assembly having an orthodontic appliance mounted thereon according to the present invention;

FIG. 2 is an exploded perspective view of the bracket, mounting pad and appliance shown in FIG. 1;

FIG. 3 is a top plan view of the bracket and pad assembly and the appliance shown in FIG. 1 and taken substantially along line 3—3 thereof;

FIG. 4 is a front elevational view of a bracket and pad assembly with a modified orthodontic appliance according to the present invention;

FIG. 5 is a front elevational view of the appliance in FIG. 4 but prior to mounting on a bracket and pad assembly;

FIG. 6 is a front elevational view of a bracket and pad assembly together with a further modified orthodontic appliance according to the present invention;

FIG. 7 is a front elevational view of the orthodontic appliance shown in FIG. 6 but prior to mounting on a bracket and pad assembly;

FIG. 8 is a still further modified orthodontic appliance according to the present invention;

FIG. 9 is a front elevational view of a bracket and pad assembly together with a further modified orthodontic appliance according to the present invention;

FIG. 10 is a side or end elevational view of FIG. 9 taken substantially along line 10—10 thereof;

FIG. 11 is a top plan view of FIG. 9; and

FIG. 12 is a perspective view of the orthodontic appliance shown in FIGS. 9 to 11 prior to being mounted on a bracket.

Referring now to the drawings, and particularly to FIGS. 1 to 3, the orthodontic appliance embodiment of the present invention illustrated therein is generally designated by the numeral 20 and may be termed as a force transmission arm. The arm 20 is illustrated in FIG. 1 in mounted relationship with respect to the typical bracket pad 21 having mounted thereon a typical edgewise bracket 22. For purposes of simplicity in this application, where brackets are illustrated, they are shown mounted on bracket pads or bases, but it should be appreciated that such brackets could be mounted directly onto the well known tooth bands or banding material and that the pad or the bands or the banding material are used for the purpose of attaching the brackets or appliances to the teeth of a patient. In connection with a band it circumvents the circumference of a tooth and is cemented into place, while a bracket pad or base is adhesively secured to the labial or buccal face of a tooth. It is also well known that prior to bonding a pad or base to a tooth, the appliance such as a bracket or other type of an appliance is first mounted onto the pad and usually it is spot welded to the pad. We are principally concerned here with the use of metal pads and metal brackets. However, it should be appreciated that the appliance of the present invention could be used with a plastic bracket which would be directly adhesively secured to a tooth. Moreover, the pad or base 21 would be of the usual type which would be termed a mesh pad, meaning it has a layer of mesh on the side that will be bonded to the tooth and a plate or shield layer on the side which will face the bracket or other appliance.

The bracket 22 illustrated in FIGS. 1 to 3 is commonly referred to as a Broussard bracket and includes a double tie-wing arrangement and a slot at the lingual side extending occlusogingivally of the bracket. More particularly, the bracket includes a base 25 having mesiodistally spaced apart attaching or welding flanges 26 and two pair of tie wings 27 and 28 projecting labially or buccally from the base 25. Aligned archwire slots 29 and 30 are formed in the pairs of tie wings and the slots extend mesiodistally. It can be appreciated that one or more pairs of tie wings may be provided. Further, an occlusogingivally extending slot 31 is formed on the lingual face of the base for use in mounting of suitable auxiliaries to the bracket. The bracket as illustrated in FIGS. 1 to 3 is spot welded to the base 21 and illustrated in FIG. 2 as being separated therefrom for purposes of more clearly illustrating the manner in which the present invention is mounted to the bracket and pad. For simplicity reasons, the description hereafter will refer only to a pad, but it should be appreciated that where the word pad is used it is also meant to include a band or banding material onto which the bracket may be mounted. With respect to the embodiment of FIGS. 1 to 3, it is necessary that the bracket and pad be used together in order to properly mount the orthodontic appliance 20 thereto.

The appliance 20 includes a base 34 received within the slot 31 of the bracket and between the slot and the pad 21. Extending from the base 34 is an arm 35 having a hook 36 of the free or terminal end thereof. In relation to the anatomy of the mouth, the arm 35 will normally extend gingivally and at all times essentially along the occlusogingival axis, but it should be appreciated it could extend occlusally if desired. The base 34 is formed by doubling back the respective end at the upper end of the base 34 as viewed in FIG. 1. A loop 38 is formed of a size that is a little larger than the mesiodistal width of the slot 31 so that the base cannot move downwardly as viewed in FIG. 1 relative to the bracket and pad. At the lower end of the base as viewed in FIG. 1, a tab or tail 39 is formed which also engages the bracket and particularly the lower end of the bracket to prevent upward movement of the base and appliance relative to the bracket and pad. Accordingly, the appliance 20 is held in place against occlusogingival movement relative to the bracket and pad.

The appliance 20 is mounted to the bracket and pad at the time the bracket is welded to the pad merely by placing the base of the appliance in the slot 31 of the bracket, joining the pad to the lingual face of the bracket, and then spot welding the attaching flanges 26 of the bracket to the pad. Therefore, the appliance will be mounted on the bracket and pad at the time the bracket and pad assembly is bonded to a tooth. Removal of the appliance 20 from the bracket and pad can easily be accomplished by clipping or severing the loop 38 and removing the two pieces formed, thereby leaving the slot 31 open for further use during later stages of treatment. For example, other auxiliaries can be thereafter mounted in the slot, such as an uprighting spring. It will be appreciated that the appliance 20 can be removed without the necessity of removing the entire bracket and pad assembly from the tooth. This eliminates the necessity of having to replace the bracket and pad with a further combination bracket and pad such as is the case with heretofore available appliances.

The appliance is particularly useful for the closing of spaces where the straight-wire technique is being utilized in connection with edgewise wire that is rectangular in cross section and suitably secured to the bracket in the archwire slots 29 and 30. An elastic force transmission member 42 would be attached at one end to the appliance 20, as illustrated in FIG. 1, and at the other end to another appliance which is mounted on an adjacent bracket or a bracket spaced therefrom for the purpose of applying a force between the two appliances to bring the teeth in which the brackets and appliances are mounted toward one another. By virtue of the appliance 20 being mounted centrally of the bracket and pad assembly, as shown in FIGS. 1 to 3, the application of force to the respective teeth is balanced relative to the teeth in order to provide the desired movement forces. Heretofore, the arm has been mounted on an end of the bracket which complicates the moments of force applied.

Another embodiment is shown in FIGS. 4 and 5 and generally is designated by the numeral 20A and which includes a base 45 of generally rectangular cross section having an arm 46 extending therefrom and terminating in a hooked portion 47. The base 45, as shown in FIG. 5, is bifurcated at its upper end to define tabs or tails 48 which, when the base is received in the slot of the bracket as illustrated in FIG. 4, are bendable over the upper end of the bracket to lock the appliance in place on the bracket and pad. This embodiment can be mounted in place on a bracket and pad assembly which has already been mounted on a tooth, although it can likewise be mounted on the bracket and pad assembly prior to bonding the bracket and pad assembly to the tooth. Further, the appliance 28 can easily be removed from the bracket and pad assembly without removing thereof from a tooth after its usefulness has ended by either bending the tabs 48 to their original position so that they will slide through the slot of the bracket or by clipping the hooked end from the arm 46 and moving the base of the appliance upwardly through the slot and removing same. In either event, the slot of the bracket is then opened for subsequent use in receiving other auxiliaries.

The embodiment of FIGS. 6 and 7, designated generally as 20B, differs from the embodiment of FIGS. 4 and 5 only in that a single tab is provided at the upper end of the base for holding the appliance in place on the bracket and pad assembly. More specifically, the appliance 20B includes a base 50 of generally rectangular form for fitting within the slot 31 in a relatively snug fashion. A single tab or tail 51 extends from the upper end of the base and is bendable over against the upper end of the bracket, as illustrated in FIG. 6, to lock the appliance in place on the bracket and pad. An arm 52 having a hook portion 53 extends downwardly from the base 50 in the same manner as in the other embodiments. This embodiment may be removed from the bracket and pad assembly in the same fashion as the embodiment of FIGS. 4 and 5 in that the arm may be severed to remove the hook portion so that the base can be slid upwardly and out of the slot of the bracket or the tab 51 could be bent to a straight position for removal of the appliance downwardly from the slot of the bracket. As in the other embodiments, the hooked portion may be turned to either direction depending upon the manner in which the forces are to be applied to the bracket and the tooth. By virtue of the rectangular configuration of the base 50 as with the embodiment of FIGS. 4 and 5, the appliance cannot rotate relative to the bracket and pad assembly.

Another embodiment of the invention is illustrated in FIG. 8 which is generally designated by the numeral 20C and which includes a base 56 which is generally rectangular in cross section and provided with enlargements 57 at the upper and lower ends. An arm 58 extends from the lower end of the base and terminates in a hook portion 59. This embodiment is mounted on an assembly of a base and a bracket such as of the type shown in the previous embodiments wherein the base portion 56 would be received in the slot of the bracket and the enlargements 57 would engage against the upper and lower ends of the bracket to lock the appliance in place. It is necessary to mount this appliance on the bracket at the time the bracket and pad are assembled. However, it can be easily removed by merely clipping off the enlargement at the upper end of the base and removing the pieces of the appliance from the bracket and pad assembly.

The appliance 20D can be added to an orthodontist's existing supply of brackets as can the appliances 20, 20A, 20B and 20C. Further, the appliance 20D is mounted directly on the labial or buccal face of the bracket wherein the bracket is not provided with an occlusogingivally extending slot as in the bracket 22. The bracket utilized and illustrated in FIGS. 9, 10 and 11 is identified generally as 22A and likewise includes a pair of adjacent tie wings 27A and 28A. When the bracket is assembled with the pad 21, the appliance 20D may then be mounted on the bracket by tack-welding it to the bracket. However, it should be appreciated that the appliance 20D could be mounted on the bracket prior to mounting of the bracket onto the pad.

The appliance 20D includes a base or attaching or welding flange 62 sized to fit between the adjacent pairs of tie wings 27A and 28A. An arm 63 extends from the bottom of the base 62 as viewed in FIG. 9 and terminates in a hooked portion 64. The appliance would be made of a suitable metal that would be capable of being suitably welded to the bracket. The arm 63 is provided with an offset portion 65 so that the portion of the arm designated 66 will be projecting buccally from the bracket, as illustrated in FIG. 10. Otherwise, the arm portion 66 extends along the occlusogingival axis of the bracket as in the appliances of the other embodiments. The base 62 is flattened and has a depth such that it will not interfere with the archwire which is received in the slots 29A and 29B. It can therefore be readily appreciated that the appliance 20D can easily be mounted onto a bracket in the office of the orthodontist in connection with brackets already on hand.

Further, once a total assembly, the pad, the bracket and the appliance, is mounted onto a tooth, the appliance 20D can easily be removed from the bracket without the necessity of removing the pad and bracket assembly and without interfering thereafter with the operation of the bracket. Removal can be accomplished by use of a suitable stripping pliers of the type that is used to strip a pad bonded to a tooth. The jaws of the stripping pliers are merely inserted between the base 62 of the appliance and the bracket, and the tack welds can be broken to separate the appliance from the bracket. Accordingly, the appliance 20D is removable as are the previous embodiments.

It will be appreciated that the lengths of the arms of the appliances may vary as well as the diameter of the wire used for the arms in accordance with the needs of a particular case. Any suitable length of the arm may be provided as well as any suitable wire diameter.

It will be understood that modifications and variations may be effected without departing from the scope of the novel concepts of the present invention, but it is understood that this application is to be limited only by the scope of the appended claims.

The invention is hereby claimed as follows:

1. An orthodontic appliance in combination with a bracket mountable on a band or pad, said bracket including an occlusogingivally extending slot at the face engaging the band or pad, said appliance including a base received in said slot and locked against movement when said bracket is attached to the band or pad, and an arm extending from the base with a hook on the free end thereof for receiving an elastic force transmission member, whereby the appliance is removable from the assembled bracket and band or pad by severing a portion of the appliance base.

2. The appliance defined in claim 1, wherein said means includes a doubled back portion defining portions larger than the cross section of the slot and engaging the occlusal and gingival ends of the slot.

3. The appliance defined in claim 1, wherein said base includes enlargements at the ends of the base dimensionally larger than the cross section of the slot.

4. An orthodontic appliance in combination with a bracket mountable on a band or pad, said bracket including an occlusogingivally extending slot at the face engaging the band or pad, said appliance including a base engageable in the bracket slot having a portion mating with the slot and tail means bendable against the bracket outside the slot, and an arm extending from the base along the occlusogingival axis clear of the bracket and terminating in a hook for receiving a force transmission member, whereby the appliance is removable from the assembled bracket and band or pad by severing the tail of the base.

5. The appliance defined in claim 4, wherein said tail means includes a single tail bendable against the bracket outside the slot thereof.

6. The appliance defined in claim 4, wherein said tail means includes a pair of tails bendable in opposite directions against the bracket outside the slot thereof.

7. The appliance defined in claim 1, wherein the base, arm and hook are formed from a length of wire and the base includes a doubled back portion defining means for engaging the occlusal and gingival ends of the bracket to prevent occlusogingival movement of the appliance.

8. The appliance defined in claim 1, wherein the base, arm and hook are formed from a length of wire and the base includes a doubled back portion defining a loop at one of the occlusal or gingival ends of the base larger than the cross section of the slot and a tab at the other end for engaging the bracket outside the slot, whereby clipping of the loop permits easy removal of the appliance.

9. An orthodontic appliance in combination with a bracket mountable on a band or pad, said bracket including a plurality of pairs of mesiodistally spaced tie wings, said appliance including a base for removable attachment to the bracket between adjacent pairs of tie wings, means for attaching said base to said bracket, said attaching means including tack welds that may be broken while the appliance is mounted on a tooth, and an arm extending from the base along an occlusogingival axis with a hook on the end of the arm for receiving a force transmission member.

* * * * *

UNITED STATES PATENT AND TRADEMARK OFFICE
CERTIFICATE OF CORRECTION

PATENT NO. : 4,193,195
DATED : March 18, 1980
INVENTOR(S) : Daniel A. Merkel et al.

It is certified that error appears in the above–identified patent and that said Letters Patent are hereby corrected as shown below:

Column 6, line 16, change "means" to --base--.

Signed and Sealed this

Eighth Day of July 1980

[SEAL]

Attest:

SIDNEY A. DIAMOND

Attesting Officer

Commissioner of Patents and Trademarks